United States Patent
Toth et al.

(10) Patent No.: US 8,180,131 B2
(45) Date of Patent: May 15, 2012

(54) METHODS, SYSTEMS AND COMPUTER PROGRAM PRODUCTS FOR MIXED-DENSITY OPTICAL COHERENCE TOMOGRAPHY (OCT) IMAGING

(75) Inventors: Cynthia Toth, Chapel Hill, NC (US);
Eric Buckland, Hickory, NC (US);
Bennett Groshong, Sacramento, CA (US)

(73) Assignee: Bioptigen, Inc., Durham, NC (US)

( * ) Notice: Subject to any disclaimer, the term of this patent is extended or adjusted under 35 U.S.C. 154(b) by 1017 days.

(21) Appl. No.: 12/114,166

(22) Filed: May 2, 2008

(65) Prior Publication Data
US 2008/0273783 A1    Nov. 6, 2008

Related U.S. Application Data

(60) Provisional application No. 60/927,691, filed on May 4, 2007.

(51) Int. Cl.
*A61B 6/03* (2006.01)
(52) U.S. Cl. ............... 382/131; 356/479; 356/497
(58) Field of Classification Search .......... 382/128–131; 356/450–521
See application file for complete search history.

(56) References Cited

U.S. PATENT DOCUMENTS

| | | | |
|---|---|---|---|
| 6,554,504 B2 | 4/2003 | Cook et al. | |
| 7,039,643 B2 | 5/2006 | Sena et al. | |
| 7,277,880 B1 | 10/2007 | Sekine et al. | |
| 7,277,903 B2 | 10/2007 | Petrocelli | |
| 7,298,451 B2 | 11/2007 | Fancher | |
| 7,301,644 B2 | 11/2007 | Knighton et al. | |
| 7,310,651 B2 | 12/2007 | Dave et al. | |
| 2005/0018201 A1 | 1/2005 | De Boer et al. | |
| 2005/0111720 A1 | 5/2005 | Gurcan et al. | |
| 2005/0140984 A1 | 6/2005 | Hitzenberger | |
| 2006/0171503 A1 | 8/2006 | O'Hara et al. | |
| 2006/0187462 A1 | 8/2006 | Srinivasan et al. | |
| 2007/0002327 A1 | 1/2007 | Zhou et al. | |
| 2007/0025642 A1 | 2/2007 | Buckland et al. | |
| 2007/0216909 A1 | 9/2007 | Everett et al. | |
| 2007/0258094 A1 | 11/2007 | Izatt et al. | |
| 2007/0291277 A1 | 12/2007 | Everett et al. | |
| 2008/0181477 A1 | 7/2008 | Izatt et al. | |

FOREIGN PATENT DOCUMENTS

| | | |
|---|---|---|
| WO | WO 2005/117534 A2 | 12/2005 |
| WO | WO 2006/077107 A1 | 7/2006 |

OTHER PUBLICATIONS

International Search Report and Written Opinion, PCT/US2008/005690, Aug. 20, 2008.

(Continued)

*Primary Examiner* — Edward Glick
*Assistant Examiner* — John Corbett
(74) *Attorney, Agent, or Firm* — Myers Bigel Sibley & Sajovec

(57) ABSTRACT

Methods, systems and computer program products are provided for acquiring an image set using optical coherence tomography (OCT). A first portion of a defined volume is scanned at a low-density sampling rate to obtain a plurality of low-density frames. A second portion of the defined volume is scanned at a high-density sampling rate, higher than the low-density sampling rate, to obtain at least one high-density frame. The low-density frames and the at least one high-density frame are combined to provide a complete mixed-density image set.

34 Claims, 6 Drawing Sheets

OTHER PUBLICATIONS

Choi, D. et al. Numerical Compensation of Dispersion Mismatch in Discretely Swept Optical-Frequency-Domain-Reflectometry Optical Coherence Tomography. Japanese Journal of Applied Physics vol. 45 (7) pp. 6022-6027, 2006.

Cense B. et al. Ultrahigh-resolution, high-speed, retinal imaging using spectral-domain optical coherence tomography. Optics Express vol. 12(11) pp. 2435-2447, 2004.

Choi, D. et al. Numerical Compensation of Dispersion Mismatch in Discretely Swept Optical-Frequency-Domain-Reflectometry Optical Coherence Tomography. Japanese Journal of Applied Physics vol. 45 (6) pp. 6022-6027, 2006.

Choma et al., "Sensitivity advantage of swept source and Fourier domain optical coherence tomography," Optics Express, vol. 11, No. 18, Sep. 8, 2003, 2183-2189.

Dorrer et al., "Spectral resolution and sampling issues in Fourier-transformation spectral interferometry," J. Opt. Soc. Am. B, vol. 17, No. 10, Oct. 2000, 1795-1802.

Häsler et al., "'Coherence Radar' and 'Spectral Radar'—New Tools for Dermatological Diagnosis," Journal of Biomedical Optics, vol. 3, No. 1, Jan. 1998, 21-31.

International Search Report and Written Opinion for PCT/US2006/029535; date of mailing Aug. 22, 2007.

Invitation to Pay Additional Fees and, Where Applicable, Protest Fee, International Search Report for International Application No. PCT/US2008/000673; Jul. 23, 2008.

Jiao et al., "Simultaneous acquisition of sectional and fundus ophthalmic images with spectral-domain optical coherence tomography," Optics Express, vol. 13, No. 2, Jan. 24, 2005, 444-452.

Leitgeb et al., "Performance of fourier domain vs. time domain optical coherence tomography," Optics Express, vol. 11, No. 8, Apr. 21, 2003, 889-894.

Leitgeb RA et al. Ultrahigh resolution Fourier domain optical coherence tomography. Optics Express vol. 12(10) pp. 2156-2164, 2004.

Lu, Chih-Wei et al., "Software Dispersion Compensation in Optical Coherence Tomography," Cleo/Pacific Rim 2003—The $5^{th}$ Pacific Rim Conference on Lasers and Electro-Otics, Dec. 15-29, 2003, Piscataway, NJ USA, IEEE, vol. 1, p. 127.

Mahmoud et al., "Comparison of three methods for registration of abdominal/pelvic volume data sets from functional-anatomic scans," Proc of SPIE 3979 1378-1386, 2000.

Notification of Transmittal of the International Search Report and the Written Opinion of the International Searching Authority, or the Declaration, PCT/US2008/000673; Nov. 17, 2008.

Srinivasan et al., "Three-dimensional retinal imaging with ultrahigh resolution, Fourier/spectral domain optical coherence tomography," Proc. Of SPIE 5688 (1): 90-99 (2005).

Tan-no et al., "Optical multimode frequency-domain reflectometer," Optics Letters, vol. 19, No. 8, Apr. 15, 1994, 587-589.

Wojtkowski M. et al. Ultrahigh-resolution, high-speed, Fourier domain optical coherence tomography and methods for dispersion compensation. Optics Express vol. 12 (11) pp. 2404-2422, 2004.

Yun et al., "High-speed spectral-domain optical coherence tomography at 1.3 µm wavelength," Optics Express, vol. 11, No. 26, Dec. 29, 2003, 3598-3604.

SCAN

EYE | TIME | SCAN PRESET:
[▾] | 3:08:07 PM [⇅] | MIXED 5.1 mm x 3.5mm @ 0.0, [100X100 + 1000X35] x 1 [▾] | NEW

SCAN PATTERN
○ M-MODE
○ LINEAR B-SCAN
○ RECTANGULAR VOLUME
○ RADIAL VOLUME
○ ANNULAR VOLUME
○ (MIXED VOLUME)

[LOAD LAST PARAMETERS]

INACTIVE LINES: 100

MIXED VOLUME + LINEAR

| Field | Value | Unit |
|---|---|---|
| LENGTH: | 5.1 | mm |
| WIDTH: | 3.5 | mm |
| ANGLE: | 0 | deg. |
| HORIZONTAL OFFSET: | 0 | mm |
| VERTICAL OFFSET: | 0 | mm |
| A-SCANS/B-SCAN: | 100 | LINES |
| B-SCANS/VOLUME: | 100 | FRAMES |
| NUMBER OF VOLUMES: | 1 | VOLUMES |
| HD A-SCANS/B-SCAN: | 1000 | LINES |
| HD B-SCAN FRAMES: | 35 | FRAMES |

A-SCANS/B-SCAN, B-SCANS/VOLUME: LOW DENSITY "GELATIN"

HD A-SCANS/B-SCAN, HD B-SCAN FRAMES: HIGH DENSITY

Figure 3

METHODS, SYSTEMS AND COMPUTER PROGRAM PRODUCTS FOR MIXED-DENSITY OPTICAL COHERENCE TOMOGRAPHY (OCT) IMAGING

CLAIM OF PRIORITY

The present application claims priority from U.S. Provisional Application No. 60/927,691, filed May 4, 2007, the disclosure of which is hereby incorporated herein by reference as if set forth in its entirety.

STATEMENT OF GOVERNMENT SUPPORT

This invention was made with government support under grant number 2R44EY015585 awarded by National Institutes of Health, National Eye Institute. The United States Government has certain rights in this invention.

FIELD OF THE INVENTION

The present invention relates to imaging systems and, more particularly, to optical coherence imaging systems.

BACKGROUND OF THE INVENTION

Optical Coherence Tomography (OCT) is a technique for imaging into samples, such as tissue, glass and the like. Recent advances in OCT have increased the imaging speed, allowing large image sets, such as three-dimensional volumes, to be generated relatively quickly. As OCT is typically high-speed, non-contact and non-destructive, it may be useful for imaging dynamics over short time scales, for example, well below 1.0 second, such as the beating of a heart tube in a fruit fly, and for imaging physiological changes that occur over a long time scales, for example, over days or even longer, such as over the time it takes tissues to develop or to respond to interventions.

A variety of approaches to imaging using OCT are known. Such systems may be characterized as Fourier domain OCT (ED-OCT) and time domain OCT (TD-OCT). FD-OCT generally includes swept source (SS) and spectral domain (SD), where SD systems generally use a broadband source in conjunction with a spectrometer rather than a swept laser source and a photodiode(s). TD systems generally rely on movement of a mirror or reference source over time to control imaging depth by providing coherence depth gating for the photons returning from the sample being imaged. Each system uses broadband optical sources, producing a low effective coherence that dictates the achievable resolution in the depth, or axial, direction.

These imaging techniques are derived from the general field of Optical Low Coherence Reflectometry (OLCR); the time domain techniques are derived from Optical Coherence Domain Reflectometry, swept source techniques are derived from Optical Frequency Domain Reflectometry, and spectral domain techniques have been referred to as "spectral radar."

In contrast to time domain systems, in FD-OCT the imaging depth may be determined by Fourier transform relationships between the acquired spectrum, rather than by the range of a physically scanned mirror, thereby allowing concurrent acquisition of photons from all imaged depths in the sample. Specifically, in FD-OCT, the optical frequency interval between sampled elements of the spectrum may be used to control the imaging depth, with a narrower sampling interval providing a deeper imaging capability.

The use of OCT to make accurate, quantitative measurements over time may be difficult due to the challenge of ensuring, among other things, that measurements made at different times are taken from the same place in the sample.

With the advent of FD-OCT techniques, it becomes possible to generate practical 3D images, and from these 3D images a planar en-face image. One technique for generating an en-face view and correlating depth-resolved features with landmarks observed on this en-face view are discussed in *Simultaneous acquisition of sectional and fundus ophthalmic images with spectral-domain optical coherence tomography* by Jiao et al. (24 Jan. 2005/Vol. 13, No. 2/OPTICS EXPRESS 445), the content of which is hereby incorporated herein by reference as if set forth in its entirety.

SUMMARY OF EMBODIMENTS OF THE INVENTION

Some embodiments of the present invention provide methods, systems and computer program products for acquiring an image set using optical coherence tomography (OCT). A first portion of a defined volume is scanned at a low-density sampling rate to obtain a plurality of low-density frames. A second portion of the defined volume is scanned at a high-density sampling rate, higher than the low-density sampling rate, to obtain at least one high-density frame. The low-density frames and the at least one high-density frame are combined to provide a complete mixed-density image set.

In further embodiments of the present invention, the at least one high-density frame may include a plurality of high-density frames. The first portion and the second portion of the volume may be scanned over the defined volume such that the plurality of high-density frames are separated by the plurality of low-density frames.

In still further embodiments of the present invention, the volume to be measured may be defined. A sampling density for obtaining the plurality of low-density frames and a number of low-density frames to be obtained between each of the high-density frames may be defined. A sampling density for obtaining the plurality of high-density frames and a number of high-density frames to be obtained between each of the defined number of the plurality of low-density frames may be obtained.

In some embodiments of the present invention, the number of high-density frames obtained between each of the plurality of low-density frames may be greater than one. In certain embodiments of the present invention, the number of high-density frames obtained between each of the plurality of low-density frames may include a series of contiguous high-density frames.

In further embodiments of the present invention, the high-density frames may be registered and averaged. In certain embodiments, the high-density frames may be acquired using an offset between successive frames.

In still further embodiments of the present invention, the obtained low-density frames may be registered with the at least one high-density frame to provide a single contiguous registered image.

In some embodiments of the present invention, a mixed-density volume projection intensity image may be created from the complete mixed-density image set.

In further embodiments of the present invention, total imaging duration may be from about 1.0 to about 5.0 seconds.

In still further embodiments of the present invention, the low-density sampling rate may be from about 80 frames per second to about 400 frames per second and the high-density sampling rate may be from about 10 frames per second to about 80 frames per second.

In some embodiments of the present invention, the low-density sampling rate may exceed the high density sampling rate by a factor from about 2.0 to about 10.0.

BRIEF DESCRIPTION OF THE DRAWINGS

FIG. 3 is a screen shot illustrating a mixed-density control software screen according to some embodiments of the present invention.

DETAILED DESCRIPTION OF THE INVENTION

Figure 1:
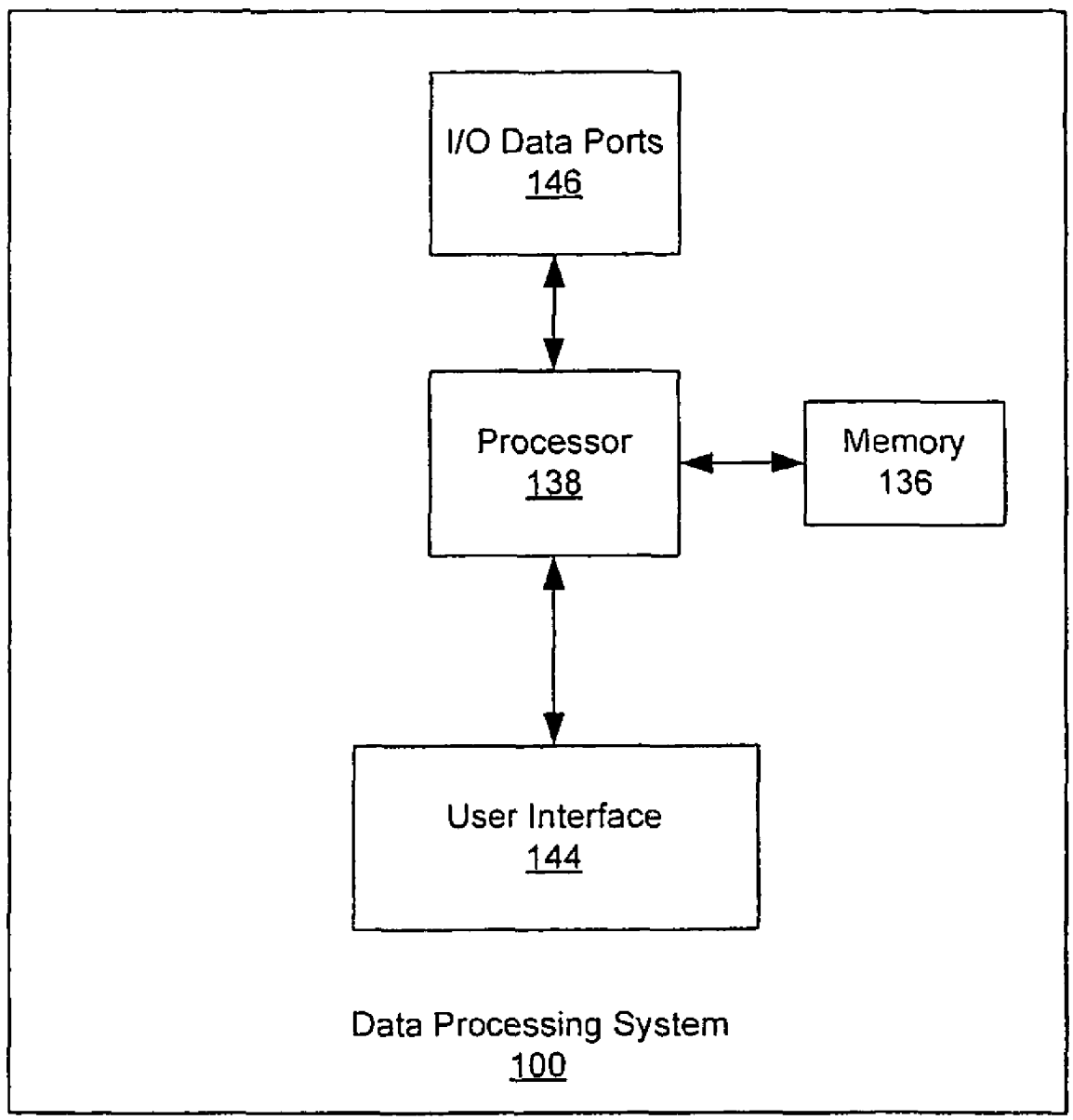
FIG. 1 is a block diagram of a data processing system according to some embodiments of the present invention.

The present invention now will be described more fully hereinafter with reference to the accompanying figures, in which embodiments of the invention are shown. This invention may, however, be embodied in many alternate forms and should not be construed as limited to the embodiments set forth herein. Like numbers refer to like elements throughout the description of the figures.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein the term "and/or" includes any and all combinations of one or more of the associated listed items.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and this specification and will not be interpreted in an idealized or overly formal sense unless expressly so defined herein.

It will be understood that, although the terms first, second, etc. may be used herein to describe various elements, these elements should not be limited by these terms. These terms are only used to distinguish one element, from another element. Thus, a first element discussed below could be termed a second element without departing from the teachings of the present invention.

The present invention may be embodied as methods, systems and/or computer program products. Accordingly, the present invention may be embodied in hardware and/or in software (including firmware, resident software, micro-code, etc.). Furthermore, the present invention may take the form of a computer program product on a computer-usable or computer-readable storage medium having computer-usable or computer-readable program code embodied in the medium for use by or in connection with an instruction execution system. In the context of this document, a computer-usable or computer-readable medium may be any medium that can contain, store, communicate, propagate, or transport the program for use by or in connection with the instruction execution system, apparatus, or device.

The computer-usable or computer-readable medium may be, for example but not limited to, an electronic, magnetic, optical, electromagnetic, infrared, or semiconductor system, apparatus, device, or propagation medium. More specific examples (a nonexhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM).

The present invention is described below with reference to block diagrams and/or flowchart illustrations of methods, systems and computer program products according to some embodiments of the invention. It is to be understood that the functions/acts noted in the blocks may occur out of the order noted in the operational illustrations. For example, two blocks shown in succession may in fact be executed substantially concurrently or the blocks may sometimes be executed in the reverse order, depending upon the functionality/acts involved.

As discussed herein, some embodiments of the present invention provide methods, systems and computer program products that generate and display two-dimensional and three-dimensional data sets derived from optical coherence tomography (OCT) data sets. The three-dimensional data sets may be displayed in an en face view, referred to herein as volume intensity projection (VIP) images. It will be understood that VIP images according to some embodiments of the present invention may also be termed summed voxel projections, Fundus images, and the like without departing from the scope of the present invention. Using methods, systems and computer program products according to some embodiments of the present invention, may improve the research and diagnostic efficacy of evaluating high quality cross sectional images by providing superior reference to surrounding structures, pathologies or topography while minimizing the time-cost of imaging, and may improve the likelihood or possibly ensure that measurements of a sample taken at different times are taken from the same or substantially the same location in the sample.

OCT imaging systems may be categorized in two general categories, time domain OCT (TD-OCT), where a moving mirror or prism in the reference arm determines the current imaging depth location in the sample, and Fourier domain OCT (FD-OCT), where there reference am is fixed in length and data is acquired over a spectrum of wavelengths to change imaging depth location in the sample. FD-OCT is typically further categorized into two categories, swept source OCT (SS-OCT) and spectral domain OCT (SD-OCT). For SS-OCT, a narrow-line width laser is typically swept in wavelength over time to interrogate the sample at different wavelengths. For SD-OCT, a broad band (low coherence) source, such as a superluminscent diode (SLD), is typically used in conjunction with a spectrometer. It will be understood that any of these or other functionally similar hardware implementations may be used to generate the data used to generate the two-dimensional, three-dimensional, and VIP images without departing from the scope of the present invention.

It will also be understood that although some embodiments of the present invention are discussed herein with respect to data sets generated using OCT imaging systems, any scanning imaging system that can obtain three-dimensional data sets may be used without departing from the scope of the present invention. For example, scanning confocal microscopy and ultrasound imaging systems may benefit from embodiments of the present invention.

OCT systems typically operate by acquiring depth data at a particular lateral position on the sample, which may be called an A-scan. The OCT beam is moved relative to the sample by any of the various depth adjustment approaches described above and another set of depth data is acquired. These series of depth images may be combined to form a 2-D image, which may be called a B-scan. Any scan pattern can generally be used without departing from the scope of the present invention. For example, commonly used scan patterns include linear and circular scan patterns. By scanning in two directions instead of just one, a three dimensional volume of data can be acquired. Again any scan pattern can generally be used to create the three dimensional image, for example, commonly used three dimensional scan patterns include rectangular, sets of radial lines, and sets of concentric circles.

OCT data is a measurement of the backscattered reflectivity at each depth in the sample at a given point. In other words, the contrast in the image is generally due to variations in the backscattered reflectivity in the sample. A desirable image set that may be extracted is a surface projection of the subsurface scattering data. One way of generating this type of image is by summing the OCT data over an A-scan. This value is the total reflectivity at that particular lateral position. By applying this over a volume scan, a 2-D image may be created. This type of image may be referred to as a Fundus image when generated from OCT data sets of retina scans. Generally, this type of image may be referred to as a VIP image. In some embodiments of the present invention, this image may be, essentially, a black and white picture of the sample.

Various exemplary embodiments of the present invention will be described herein with reference to alignment based on VIP images. As the VIP images are created from the OCT data, there is a direct correlation between pixels on the VIP image and A-scans in the OCT data set. Other algorithms to generate a useful VIP-like image may be used with some embodiments of the present invention as well, such as by summing over a limited subset of an A-scan, and/or by weighting the sum over the A-scan with some selected function suited to a particular use of the scan information.

The VIP image can be used to align the OCT system with respect to the sample in some embodiments when the VIP image is generated in nearly real time. The alignment VIP image may be acquired at a lower lateral resolution, which may increase the rate at which the VIP images are created. This image may allow the user to align the system based on OCT data, thus providing a preview of the OCT dataset. This approach in some embodiments may be more accurate than trying to visually align the sample to the OCT system or using a video camera for alignment.

It is generally desirable to acquire high-density volumetric displays that retain the maximum information content afforded by the OCT imaging modality. However, acquisition times are limited by signal-to-noise constraints, and it is generally not practical to acquire maximum-density images in a short enough time frame to freeze artifacts of motion associated with living biological subjects. For example, in a typical high performance spectral domain OCT system, axial A-scan lines with an isotropic resolution of 10 micrometers may be acquired at a rate of 20,000 lines per second. At this rate it takes 16 seconds to acquire uniformly sampled subject area of 100 square millimeters (with 318096 lines, at 564 lines×564 frames sampling).

Alternatively, a low-density image, effectively undersampled by a factor of 10 can be acquired in about 1.6 seconds with 178 lines×178 frames sampling. The degree of undersampling improves as the sampled area decreases.

Current systems are limited by the need to trade off the need for high resolution with the need for rapid acquisition. A typical commercial scan sequence provides 300 lines×180 frames in a 36 square millimeter area. This imaging configuration results in slightly undersampled lines, by about 12% but may depend on actual resolution, and results in greater undersampling in the frame direction. The average image is undersampled by a factor of two.

In other words, higher resolution images are not acquired at an optimal speed. Low-resolution images may be acquired much faster, but are by definition not as good. Current systems for acquiring image data sets try to balance the desire for high resolution images and the need for rapid acquisition. One method of obtaining an image calls for acquisition of both OCT images and non-OCT images. The OCT images are registered to non-OCT images, however, acquisition of two types of images may require two different systems. For example, the non-OCT image may be a scanning laser opthalmascope image or photographic video fundus image, which is acquired with different systems than the OCT system. Another approach for acquiring an image is to use eye tracking. One beam is used to identify and maintain position and another beam is used to obtain the OCT image and holds it in place. However, this method requires two simultaneous radiant beams on the eye, which can be difficult to implement, require a relatively slow feedback loop and increase the radiant power incident on the eye.

Thus, some embodiments of the present invention provide methods, systems and computer program products configured to obtain a mixed-density image that may be acquired in a relatively short period of time, but also has a much higher resolution than conventional imaging techniques as will be discussed further below with respect to FIGS. 1 through 7. According to some embodiments of the present invention, only OCT images are acquired, which reduces the amount of equipment needed to obtain the image. Furthermore, the images produced in accordance with some embodiments of the present invention may not suffer from any distortions, which may also be an improvement over conventional methods.

Some embodiments of the present invention provide methods, systems and computer program products for acquiring mixed-density image sets using optical coherence tomography (OCT). A first portion of a defined volume is scanned at a low-density sampling rate to obtain a plurality of low-density frames. As used herein, a low-density sampling rate refers to a sampling rate of from about 80 frames per second to about 400 frames per second, where a frame consists of a number of lines of data, and the number of lines per frame generally varies from about 100 to about 500, and lines are typically acquired at a rate of from 15,000 lines per second to about 60,000 lines per second in ophthalmic applications. A low density frame may or may not be undersampled with respect to the lateral resolution of the optical system. In a typical implementation, a low density frame is effectively undersampled by a factor of about two to five. A second portion of the defined volume is scanned at a high-density sampling rate, higher than the low-density sampling rate, to obtain at least one high-density frame. As used herein, a high-density sampling rate refers to a sampling rate of from about 10 to about 80 where the number of lines per frame generally varies from about 250 to about 2500. A high density frame may or may not be oversampled with respect to the lateral resolution of the optical system. In a typical implementation, a high density frame is optimally sampled or effectively oversampled by a factor of about two. The low-density frames and the at least one high-density frame are combined to provide a complete mixed-density image set. In some embodiments, scanning may include scanning over the defined volume such that the high-density frames are separated by low-density frames as will be discussed further herein with respect to FIGS. 1 through 7. The mixed density image set may be used to create a mixed-density VIP image. A total imaging duration according to some embodiments of the present invention may be from about 1.0 seconds to about 5.0 seconds.

Referring first to FIG. 1, an exemplary embodiment of a data processing system 100 suitable for use in an OCT system in accordance with some embodiments of the present invention will be discussed. The data processing system 100 typically includes a user interface 144, such as a keyboard, keypad, touchpad or the like, P/O data ports 146 and a memory 136 that communicate with a processor 138. The I/O data ports 146 can be used to transfer information between the data processing system 100 and another computer system or a network. These components may be conventional components, such as those used in many conventional data processing systems, which may be configured to operate as described herein.

Figure 2:
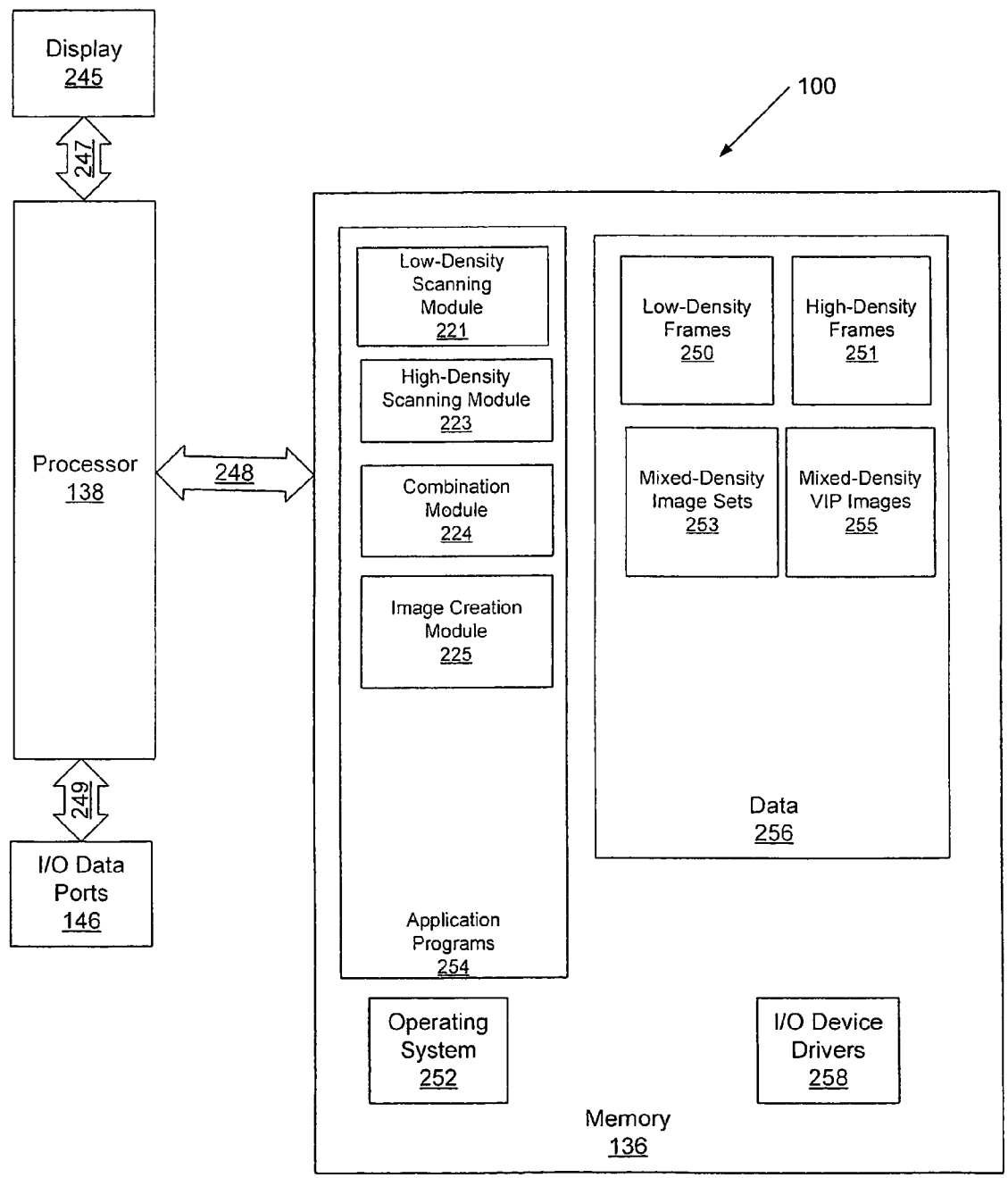
FIG. 2 is a more detailed block diagram of data processing systems according to some embodiments of the present invention.

Referring now to FIG. 2, a more detailed block diagram of the data processing system 100 in accordance with some embodiments of the present invention will be discussed. The processor 138 communicates with a display 245 via and address/data bus 247, the memory 136 via an address/data bus 248 and the I/O data ports 146 via an address/date bus 249. The processor 138 can be any commercially available or custom microprocessor. The memory 136 is representative of the overall hierarchy of memory devices containing the software and data used to implement the functionality of the data processing system 100. The memory 136 can include, but is not limited to, the following types of devices: cache, ROM, PROM, EPROM, EEPROM, flash memory, SRAM, and DRAM.

As shown in FIG. 2, the memory 136 may include several categories of software and data used in the data processing system 100: an operating system 252; application programs 254; input/output (I/O) device drivers 258; and data 256. As will be appreciated by those of skill in the art, the operating system 252 may be any operating system suitable for use with a data processing system, such as OS/2, AIX or zOS from International Business Machines Corporation, Armonk, N.Y., Windows95, Windows98, Windows2000, WindowsXP, or Vista from Microsoft Corporation, Redmond, Wash., Unix, Linux, or a real-time operating system such as QNX or VxWorks, or the like. The I/O device drivers 258 typically include software routines accessed through the operating system 252 by the application programs 254 to communicate with devices such as the I/O data port(s) 146 and certain memory 136 components. The application programs 254 are illustrative of the programs that implement the various features of the data processing system 100 included in an FDOCT system and preferably include at least one application that supports operations according to some embodiments of the present invention. Finally, the data 256 represents the static and dynamic data used by the application programs 254, the operating system 252, the I/O device drivers 258, and other software programs that may reside in the memory 136.

As illustrated in FIG. 2, the data 256 according to some embodiments of the present invention may include low-density frames 250, high-density frames 251, mixed density image sets 253 and mixed density VIP images 255. Although the data 256 illustrated in FIG. 2 includes four different files 250, 251, 253 and 255, embodiments of the present invention are not limited to this configuration. Two or more files may be combined to make a single file, a single file may be split into two or more files and the like without departing from the scope of the present invention.

As further illustrated in FIG. 2, the application programs 254 may include a low-density scanning module 221, a high-density scanning module 223, a combination module 224 and an image creation module 225 according to some embodiments of the present invention. While the present invention is illustrated, for example, with reference to the low-density scanning module 221, the high-density scanning module 223, the combination module 224 and the image creation module 225 being application programs in FIG. 2, as will be appreciated by those of skill in the art, other configurations may also be utilized while still benefiting from the teachings of the present invention. For example, the low-density scanning module 221, the high-density scanning module 223, the combination module 224 and the image creation module 225 may also be incorporated into the operating system 252 or other such logical division of the data processing system 100. Thus, the present invention should not be construed as limited to the configuration of FIG. 2, but is intended to encompass any configuration capable of carrying out the operations described herein.

Furthermore, while the low-density scanning module 221, the high-density scanning module 223, the combination module 224 and the image creation module 225 are illustrated in a single data processing system, as will be appreciated by those of skill in the art, such functionality may be distributed across one or more data processing systems. Thus, the present invention should not be construed as limited to the configuration illustrated in FIGS. 1 through 2, but may be provided by other arrangements and/or divisions of function between data processing systems.

In particular, the low-density scanning module 221 is configured to scan a first portion of a defined volume at a low-density sampling rate to obtain a plurality of low-density frames 250. In some embodiments of the present invention, the low-density scanning module 221 may be configured to scan the defined volume at the low-density sampling rate of from about 80 frames per second to about 400 frames per second. The high-density scanning module 223 is configured to scan a second portion of the defined volume at a high-density sampling rate, higher than the low-density sampling rate, to obtain at least one high-density frame 251. In some embodiments of the present invention, the high-density scanning module may be configured to scan the defined volume at the high-density sampling rate of from about 10 frames per second to about 80 frames per second.

In some embodiments of the present invention, the at least one high-density frame comprises a plurality of high-density frames. In these embodiments, the mixed density scanning may be performed in such a way that each plurality of high-density frames is separated by a plurality of low-density frames. The volume to be measured may be defined by the user. Before the volume is scanned, the low-density scanning module 221 may be configured to define the low-density sampling rate for obtaining the plurality of low-density frames and a number of the plurality of low-density frames to be obtained between each of the high-density frames. In other words, a user may set how many frames will be sampled at the low-density sampling rate before a (plurality of) high-density frame(s) are obtained. The high-density scanning module 223 may similarly be configured to define the high-density sampling rate for obtaining the plurality of high-density frames and a number of the plurality of high-density frames to be obtained between each of the defined number of the plurality of low-density frames. One or more high-density frames may be obtained between the defined number of low-density frames.

In some embodiments of the present invention, the plurality of high-density frames obtained between each of the plurality of low-density frames comprises a series of contiguous high-density frames. The high-density scanning module 223 may be configured to scan the second portion of the defined volume to provide the series of contiguous high-density frames by acquiring the plurality of high-density frames using an offset between successive frames, and registering and averaging the acquired plurality of high-density frames into one or more averaged high density frames.

In particular, in some embodiments, a multiplicity of high-density frames may be registered and averaged to create a lower noise high density frame. In other words, the at least one high-density frame can actually be a combination of a series of frames or a sequence of contiguous high density frames. In these embodiments, a signal-to-noise of cross sectional images may be improved for select regions of the image by registration and averaging of a finite number of successive frames acquired at substantially the same subject location. In addition, signal-to-noise of cross sectional images may be further improved for select regions of the image by registration and averaging of a finite number of successive frames acquired by dithering an offset between successive frames, such that the offset is a small fraction of the programmed inter-frame distance (i.e., low density inter-frame distance) but larger than a distance that is approximately the wavelength of light used for imaging as will be discussed further below.

Registration is discussed in detail in commonly assigned U.S. patent application Ser. No. 11/461,083, filed Jul. 31, 2006 entitled *Methods, Systems And Computer Program Products For Analyzing Three Dimensional Data Sets Obtained From A Sample*, the disclosure of which is hereby incorporated herein by reference as if set forth in its entirety.

The combination module 224 may be configured to combine the low-density frames and the at least one high-density frame to provide a complete mixed-density image set 253. In some embodiments, the combination module 224 may be configured to register the obtained low-density frames with the at least one high-density frame to provide a single contiguous registered image. The image creation module 225 may be configured to create a mixed-density VIP image 255 from the complete mixed-density image set according to some embodiments of the present invention. The total imaging duration may be from about 1.0 to about 5.0 seconds.

It will be understood that systems in accordance with some embodiments of the present invention may be configured to transition between low-density mode of operation of the low-density scanning module and high-density mode of operation of the high-density scanning module smoothly such that spatial registration between successive frames is maintained as will be discussed further below.

As discussed above with respect to FIGS. 1 and 2, some embodiments of the present invention provide methods for acquiring three-dimensional data sets with a plurality of lateral image densities from a sample. A mixed-density en-face view, referred to herein as a VIP image, is created from the three-dimensional data set. The mixed-density VIP image is displayed with appropriate scaling such that high lateral image density and low lateral image density regions of the VIP display integrate to regular two-dimensional display representative of the VIP image of the subject.

The low-density images form a uniformly distributed encapsulating volume, matrix, or connective frame that provides reference for the high-density scans. Regions of disparate scan density may be aligned, or registered, using a cross-correlation function for optimizing the overlap of successive scan frames that form the boundaries.

The high-density image may be acquired for one or more cross-sectional portions of the image, and embedded in a low-density image. The high-density cross sections may be positioned by default or by user selection, and may include averaged or non-averaged frames.

Some embodiments of the present invention provide methods for setting the acquisition parameters in order to capture a relatively high-speed, low-density image that acts as a reference volume for the visualization of a more detailed high-density cross sections.

As discussed above, in accordance with some embodiments of the present invention total imaging duration may be constrained to a time relevant to the subject, and the total imaging duration may be divided to optimize the quality of the detailed high-density image, and the remaining imaging duration may be assigned to, and constrains the density of, the low-density encapsulating volume.

Figure 4:
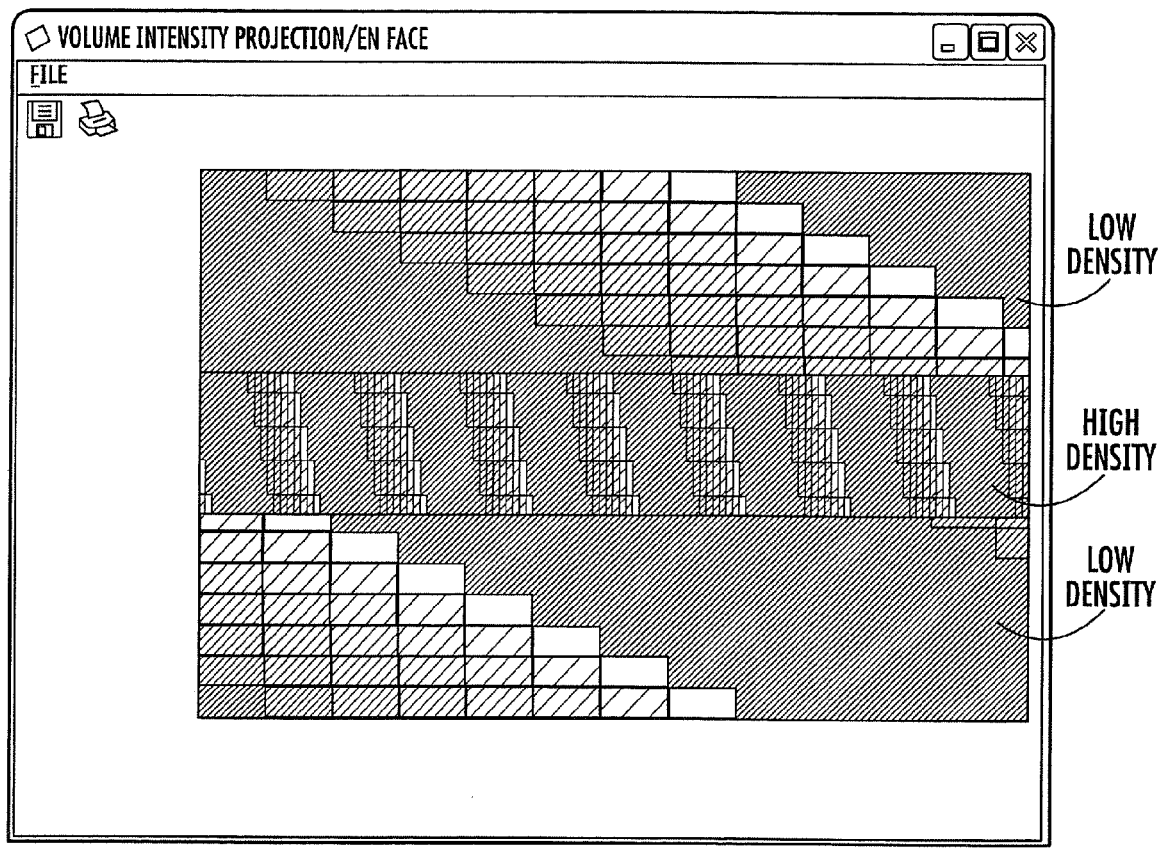
FIG. 4 is a target representation of a mixed-mode en face (VIP) image according to some embodiments of the present invention.

Some embodiments of the present invention will now be discussed with respect to FIGS. 3 and 4. In particular, FIG. 3 is a screen shot illustrating a mixed-density control software screen 300 according to some embodiments of the present invention. FIG. 4 is a target representation 400 of a mixed-mode en face (VIP) image according to some embodiments of the present invention.

The primary objectives for any sampling sequence can be summarized as follows: a) Obtain at least one high resolution, low noise, optimally sampled or oversampled, cross sectional image that captures target pathology; b) obtain a volume image surrounding the high-density cross-section(s) to provide accurate location reference for the high-resolution cross-section(s), as, for example, may be observed from the en face view provided in a VIP display; and c) acquire the total image set rapidly as appropriate for the subject under test, for example, between less than about 1.0 seconds and no more than about 5.0 seconds for imaging of the retina in an adult human.

An exemplary imaging sequence will now be discussed with respect to FIGS. 1 through 4. The exemplary imaging sequence that illustrates the point is the capture and averaging of a co-located series of ten 1000 line frames, captured in 1.0 second, within a low-density volume captured in 1.0 second, for a total imaging time of two seconds. In this example, the scanning sequence is structured such that 70 frames of 140 lines are acquired in approximately one-half second, undersampled by approximately a factor of 16 using the low-density module 221. At the mid-point of the image, the scan density changes to 1000 lines, oversampled by a factor of two by the high-density module 223. In particular, a plurality of 10 scans in the mid-point location may be taken, registered laterally using cross-correlation techniques known in the art, and averaged. This acquisition period may be approximately 1.0 second. The remaining 50% of the volume may be scanned at the set low-density sampling rate and acquired in the remaining half-second by the low-density module 221. The low-density volume when presented in an en face (VIP)

display 400 illustrated in FIG. 4 may be very adequate for the presentation of major pathological features, such as blood vessels and optic nerve head, and quite satisfactory for registration of the high resolution cross-sectional image. The 2× oversampled and averaged cross-sectional image can provide a high quality image for investigating the detailed embedded pathology.

It may also be advantageous to step the lateral frame position of the sequential high-density frames to reduce coherent speckle noise, enhancing the quality of frame-averaged images. The inter-frame displacement may be on the order of the source wavelength, but substantially less than the lateral resolution of the imaging system. This is readily accomplished in ocular imaging, where the wavelength may be approximately 1.0 micrometer and the resolution may be from about 10 to about 20 micrometers.

A number of technological developments may be utilized to realize the mixed-density scanning mode in accordance with some embodiments of the present invention. For example, the scan controller may be configured to switch smoothly between high speed low-density modes and the slower speed high resolution modes while maintaining spatial registration between successive boundary frames. The frame-stepping cross-sectional display may be configured to switch smoothly between representation of frames of different line counts. The en face (VIP) display may be able to seamlessly project a correctly scaled lateral view with areas of different density. A display strategy may be implemented that allows binding the averaged high-density frames into one display frame, both in cross-section and en face, or in a plurality of display frames. The interfaces between low- and high-density regions may be correctly pixel registered at the boundaries. Three-dimensional viewing technology may accommodate the different densities, and allow for frame-to-frame cross-sectional registration both within regions of a density, and at the boundaries or interfaces between them, even when the pixel counts at the interfaces are mismatched.

Although the VIP image 400 of FIG. 4 illustrates one high-density imaging frame set embedded in the middle of a low-density "gelatin", embodiments of the present invention are not limited to this configuration. For example, the concept is readily extended to any plurality of high-density frame-sets embedded at various locations within the low density "gelatin", i.e. plurality of connective frames. Furthermore, the concept may be extended to the development of a plurality of "gelatinous" densities throughout the imaging reason. A motivation for this is, for example, to increase the density in the regions nearest to pathology of interest, while maintaining reference to the broader landscape. For example, a three-stage image may be desirable, where the outer section is undersampled by a factor of ten, a mid-section is undersampled by a factor of two, and a high-density region is oversampled by a factor of two. It will be understood that the high-density region(s) need not be collocated, but may instead encompass one or more extended regions without deviating from the scope of the invention.

Furthermore, it will be understood that the scan patterns need not be simple linear cross-sections (B-scans) acquired frame-wise into a rectangular volume. Alternative modes may be adopted, for example, radial scans, and annular scans, among others, without loss of generality without departing from the scope of the present invention.

Additionally, while embodiments according to the invention are discussed herein with specific consideration towards Fourier-domain OCT, which by implementation has a line-priority image acquisition sequence (axial lines are assembled into frames which are assembled into volumes), other image sequences are envisioned as well. For example, in time-domain OCT (TD-OCT), pixels may be assembled into axial lines at a lateral position that may then be assembled into frames, or may be assembled first into lateral frames (C-scans) and then frames assembled by depth. This invention may be equally applied to varying the acquisition density of the C-scans.

Image processing using FDOCT is discussed in commonly assigned U.S. patent application Ser. No. 12/016,352, filed Jan. 18, 2008 entitled *Methods, System and Computer Program Products for Processing Images Generated Using Fourier Domain Optical Coherence Tomography (FDOCT)*, the disclosure of which is hereby incorporated herein by reference as if set forth in its entirety herein.

Figure 5:
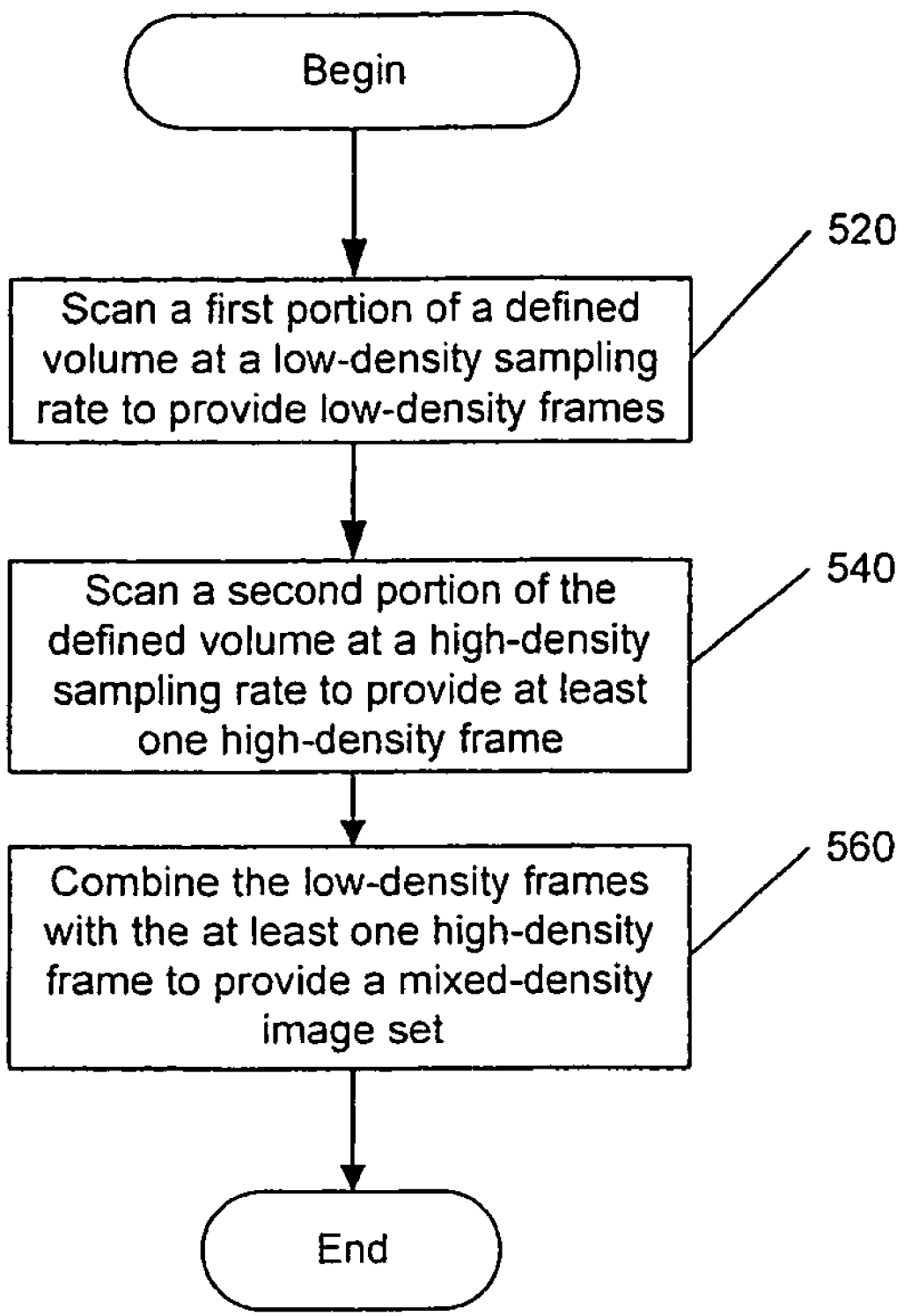
FIGS. 5 through 7 are flowcharts illustrating operations according to various embodiments of the present invention

Operations of for acquiring mixed density image sets using OCT systems according to various embodiments of the present invention will now be discussed with respect to the flowcharts of FIGS. 5 through 7. Referring first to FIG. 5, operations for acquiring an image set using optical coherence tomography (OCT) begin at block 520 by scanning a first portion of a defined volume at a low-density sampling rate to obtain a plurality of low-density frames. A second portion of the defined volume is scanned at a high-density sampling rate, higher than the low-density sampling rate, to obtain at least one high-density frame (block 540). The low-density frames and the at least one high-density frame are combined to provide a complete mixed-density image set (block 560).

Figure 6:
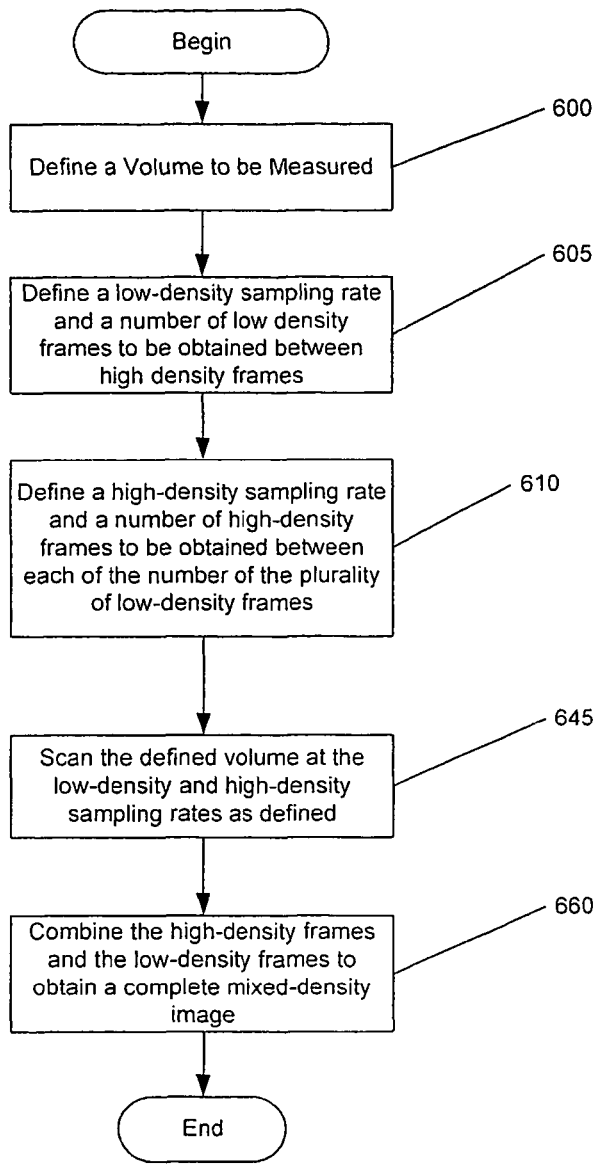

Referring now to FIG. 6, operations begin at block 600 by defining the volume to be measured. The low-density sampling rate for obtaining the plurality of low-density frames and a number of the plurality of low-density frames to be obtained between each of the high-density frames may also be defined (block 605). In some embodiments of the present invention, the low-density sampling rate may be from about 80 frames per second to about 400 frames per second. The high-density sampling rate for obtaining the plurality of high-density frames and a number of the plurality of high-density frames to be obtained between each of the defined number of the plurality of low-density frames may be defined (block 610). In some embodiments of the present invention, the high-density sampling rate may be from about 10 frames per second to about 80 frames per second.

A first portion of a defined volume may be scanned at a low-density sampling rate to obtain a plurality of low-density frames and a second portion of the defined volume may be scanned at a high-density sampling rate, higher than the low-density sampling rate, to obtain at least one high-density frame (block 645). In some embodiments, the at least one high density frame includes a plurality of high-density frames. In these embodiments, the defined volume may be scanned such that the one or more high-density frames are separated the defined number plurality of low-density frames. As discussed above, in some embodiments the number of high-density frames obtained between each of the plurality of low-density frames may be a series of contiguous high-density frames.

The low-density frames and the at least one high-density frame are combined to provide a complete mixed-density image set (block 660). In some embodiments, the obtained low-density frames may be registered with the at least one high-density frame to provide a single contiguous registered image. For example, a mixed-density volume projection intensity image may be created from the complete mixed-density image set. Thus, according to some embodiments of the present invention, an image have an improved resolution and a total imaging duration from about 1.0 to about 5.0 seconds.

Figure 7:
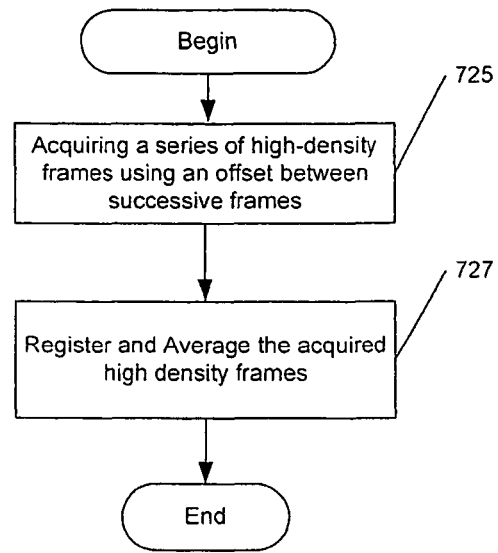

Referring now to FIG. 7, operations for scanning the second portion of the defined volume to provide the series of contiguous high-density frames will be discussed. As illustrated in FIG. 7, operations begin at block 725 by acquiring the high-density frames using an offset between successive frames. In some embodiments, the high-density frames may be registered and averaged (block 727).

In the drawings and specification, there have been disclosed embodiments of the invention and, although specific terms are employed, they are used in a generic and descriptive sense only and not for purposes of limitation, the scope of the invention being set forth in the following claims.

That which is claimed is:

1. A method of acquiring an image set using optical coherence tomography (OCT), comprising:
    defining a contiguous scanning sequence structured to acquire at least two portions of a defined volume;
    scanning a first portion of the at least two portions of the defined volume at a low-density sampling rate to obtain a plurality of low-density frames;
    scanning a second portion of the at least two portions of the defined volume at a high-density sampling rate, higher than the low-density sampling rate, to obtain at least one high-density frame; and
    registering the low-density frames and the at least one high-density frame to provide a complete mixed-density image set.

2. The method of claim 1:
    wherein the at least one high-density frame comprises a plurality of high-density frames; and
    wherein scanning a first portion and scanning a second portion comprises scanning over the defined volume such that the plurality of high-density frames are separated by the plurality of low-density frames.

3. The method of claim 2, wherein scanning the first portion is preceded by:
    defining the volume to be measured;
    defining a sampling density obtaining the plurality of low-density frames;
    defining a number low-density frames to be obtained between each of the high-density frames;
    defining a sampling density for obtaining the plurality of high-density frames; and
    defining a number of high-density frames to be obtained between each of the defined number of the plurality of low-density frames.

4. The method of claim 3, wherein the number of high-density frames obtained between each of the plurality of low-density frames is greater than one.

5. The method of claim 4, wherein the number of high-density frames obtained between each of the plurality of low-density frames comprises a series of contiguous high-density frames.

6. The method of claim 5, wherein scanning the second portion of the defined volume to provide the series of contiguous high-density frames further comprises registering and averaging the acquired high-density frames.

7. The method of claim 6, wherein scanning the second portion of the defined volume to provide the series of contiguous high-density frames further comprises acquiring the high-density frames using an offset between successive frames.

8. The method of claim 1, wherein the registering comprises registering the obtained low-density frames with the at least one high-density frame to provide a single contiguous registered image.

9. The method of claim 1, further comprising creating a mixed-density volume projection intensity image from the complete mixed-density image set.

10. The method of claim 1, wherein total imaging duration is from about 1.0 to about 5.0 seconds.

11. The method of claim 1, wherein the low-density sampling rate is from about 80 frames per second to about 400 frames per second and wherein the high-density sampling rate is from about 10 frames per second to about 80 frames per second.

12. The method of claim 1, wherein the high-density sampling rate exceeds the low density sampling rate by a factor from about 2.0 to about 10.0.

13. The method of claim 1, wherein defining comprises defining the contiguous scanning sequence without any feedback from the image.

14. A optical coherence tomography (OCT) system for acquiring a mixed density image set, comprising:
    at least one processor configured to pre-define a contiguous scanning sequence structured to acquire at least two portions of a defined volume before the defined volume is scanned, the at least one processor including:
    a low-density scanning module configured to scan a first portion of the at least two portions of the defined volume at a low-density sampling rate to obtain a plurality of low-density frames;
    a high-density scanning module configured to scan a second portion of the at least two portions of the defined volume at a high-density sampling rate, higher than the low-density sampling rate, to obtain at least one high-density frame; and
    a combination module configured to register the low-density frames and the at least one high-density frame to provide a complete mixed-density image set.

15. The system of claim 14:
    wherein the at least one high-density frame comprises a plurality of high-density frames; and
    wherein the high-density scanning module and the low-density scanning module are further configured to scan over the defined volume such that the plurality of high-density frames are separated by the plurality of low-density frames.

16. The system claim 15:
    wherein the low-density scanning module or the high-density scanning module is further configured to define the volume to be measured;
    wherein the low-density scanning module is configured to define a sampling density for obtaining the plurality of low-density frames and a number of low-density frames to be obtained between each of the high-density frames; and
    wherein the high-density scanning module is configured to define a sampling density for obtaining the plurality of high-density frames and a number of high-density frames to be obtained between each of the defined number of the plurality of low-density frames.

17. The system of claim 16, wherein the number of high-density frames obtained between each of the plurality of low-density frames comprises a series of contiguous high-density frames.

18. The system of claim 17, wherein the high-density scanning module is further configured to scan the second portion of the defined volume to provide the series of contiguous high-density frames by registering and averaging the acquired high-density frames.

19. The system of claim 18, wherein the high-density scanning module is further configured to scan the second portion of the defined volume to provide the series of contiguous high-density frames by acquiring the high-density frames using an offset between successive frames.

20. The system of claim 14, wherein the combination module is further configured to register the obtained low-density frames with the at least one high-density frame to provide a single contiguous registered image.

21. The system of claim 14, further comprising an image creation module configured to create a mixed-density volume projection intensity image from the complete mixed-density image set.

22. The system of claim 14, wherein total imaging duration is from about 1.0 to about 5.0 seconds.

23. The system of claim 14, wherein the low-density scanning module is configured to scan the defined volume at the low-density sampling rate of from about 80 frames per second to about 400 frames per second and wherein the high-density scanning module is configured to scan the defined volume at the high-density sampling rate of from about 10 frames per second to about 80 frames per second.

24. The system of claim 14, wherein the high density sampling rate exceeds the low density sampling rate by a factor from about 2.0 to about 10.0.

25. The system of claim 14, wherein the system is configured to transition between low-density mode of operation of the low-density scanning module and high-density mode of operation of the high-density scanning module smoothly such that spatial registration between successive frames is maintained.

26. The system of claim 14, wherein the processor is further configured to define the contiguous scanning sequence without any feedback from the image.

27. A computer program product for acquiring an image set using optical coherence tomography (OCT), the computer program product comprising:
a non-transitory computer-readable storage medium having computer-readable program code embodied in the medium, the computer-readable program code comprising:
computer readable program code configured to define a contiguous scanning sequence structured to acquire at least two portions of a defined volume before the defined volume is scanned;
computer readable program code configured to scan a first portion of a defined volume at a low-density sampling rate to obtain a plurality of low-density frames;
computer readable program code configured to scan a second portion of the defined volume at a high-density sampling rate, higher than the low-density sampling rate, to obtain at least one high-density frame; and
computer readable program code configured to register the low-density frames and the at least one high-density frame to provide a complete mixed-density image set.

28. The computer program product of claim 27:
wherein the at least one high-density frame comprises a plurality of high-density frames; and
wherein computer readable program code configured to scan a first portion and a second portion comprises computer readable program code configured to scan over the defined volume such that the plurality of high-density frames are separated by the plurality of low-density frames.

29. The computer program product of claim 28, further comprising:
computer readable program code configured to define the volume to be measured;
computer readable program code configured to define a sampling density for obtaining the plurality of low-density frames;
computer readable program code configured to define a number of low-density frames to be obtained between each of the high-density frames;
computer readable program code configured to define a sampling density for obtaining the plurality of high-density frames; and
computer readable program code configured to define a number of high-density frames to be obtained between each of the defined number of the plurality of low-density frames.

30. The computer program product of claim 29, wherein the number of high-density frames obtained between each of the plurality of low-density frames comprises a series of contiguous high-density frames.

31. The computer program product of claim 30, wherein the computer readable program code configured to scan the second portion of the defined volume to provide the series of contiguous high-density frames further comprises computer readable program code configured to register and average the acquired high-density frames.

32. The computer program product of claim 30, wherein the computer readable program code configured to scan the second portion of the defined volume to provide the series of contiguous high-density frames further comprises computer readable program code configured to acquire the high-density frames using an offset between successive frames.

33. The computer program product of claim 27, further comprising computer readable program code configured to create a mixed-density volume projection intensity image from the complete mixed-density image set.

34. The computer program product of claim 27, wherein the computer readable program code configured to define further comprises computer readable program code configured to define the contiguous scanning sequence without any feedback from the image.

* * * * *

UNITED STATES PATENT AND TRADEMARK OFFICE
CERTIFICATE OF CORRECTION

| | |
|---|---|
| PATENT NO. | : 8,180,131 B2 |
| APPLICATION NO. | : 12/114166 |
| DATED | : May 15, 2012 |
| INVENTOR(S) | : Toth et al. |

Page 1 of 1

It is certified that error appears in the above-identified patent and that said Letters Patent is hereby corrected as shown below:

In the Patent:
Column 1, Background of the Invention: Line 42:
  Please correct "(ED-OCT)" to read -- (FD-OCT) --

Column 4, Line 56: Please correct "am is" to read -- arm is --

Signed and Sealed this
Sixth Day of November, 2012

David J. Kappos
*Director of the United States Patent and Trademark Office*